US009049879B2

(12) United States Patent
Bhargava

(10) Patent No.: US 9,049,879 B2
(45) Date of Patent: *Jun. 9, 2015

(54) EDIBLE ENERGY COMPOSITION

(75) Inventor: Manoj Bhargava, Farmington Hills, MI (US)

(73) Assignee: International IP Holdings LLC, Bloomfield Hills, MI (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/470,462

(22) Filed: May 14, 2012

(65) Prior Publication Data

US 2012/0277179 A1    Nov. 1, 2012

Related U.S. Application Data

(63) Continuation-in-part of application No. 12/139,163, filed on Jun. 13, 2008, now Pat. No. 8,187,647.

(51) Int. Cl.

| | | |
|---|---|---|
| *A23L 1/236* | (2006.01) | |
| *A23L 1/03* | (2006.01) | |
| *A23L 1/22* | (2006.01) | |
| *A23L 1/30* | (2006.01) | |
| *A23L 1/302* | (2006.01) | |
| *A23L 1/305* | (2006.01) | |

(52) U.S. Cl.
CPC ............ *A23L 1/2367* (2013.01); *A23L 1/0325* (2013.01); *A23L 1/22* (2013.01); *A23L 1/30* (2013.01); *A23L 1/3002* (2013.01); *A23L 1/302* (2013.01); *A23L 1/3051* (2013.01); *A23V 2002/00* (2013.01); *A23V 2200/33* (2013.01)

(58) Field of Classification Search
CPC ......... A23L 2/00; A23L 1/3051; A23L 1/302; A23L 1/236; A23L 1/30; A23V 2200/33; A23V 2250/0644
USPC .................................... 426/72, 590, 594, 656
See application file for complete search history.

(56) References Cited

U.S. PATENT DOCUMENTS

| | | | |
|---|---|---|---|
| 5,397,786 A | 3/1995 | Simone | |
| 5,760,005 A | 6/1998 | Iwatschenko et al. | |
| 6,261,589 B1 * | 7/2001 | Pearson et al. | 424/439 |
| 8,187,647 B2 * | 5/2012 | Bhargava | 426/72 |
| 2001/0043957 A1 | 11/2001 | Mann | |
| 2002/0102345 A1 | 8/2002 | Ramirez | |
| 2002/0136782 A1 | 9/2002 | Fleischner | |
| 2002/0176881 A1 | 11/2002 | Verlaan et al. | |
| 2003/0219500 A1 | 11/2003 | Howard et al. | |
| 2004/0071825 A1 | 4/2004 | Lockwood | |
| 2004/0096547 A1 | 5/2004 | Ferruzzi | |
| 2005/0031651 A1 | 2/2005 | Gervais et al. | |
| 2006/0286181 A1 | 12/2006 | Gardiner et al. | |
| 2007/0224292 A1 | 9/2007 | Brunner et al. | |
| 2010/0285179 A1 * | 11/2010 | Bhargava | 426/72 |
| 2012/0135113 A1 * | 5/2012 | Bhargava | 426/72 |

FOREIGN PATENT DOCUMENTS

| | | |
|---|---|---|
| GB | 2285578 A | 7/1995 |
| JP | 2005527234 A1 | 9/2005 |
| WO | WO8808259 A1 | 11/1988 |
| WO | WO0062812 A1 | 10/2000 |
| WO | WO03079818 A1 | 10/2003 |
| WO | WO2005018344 A1 | 8/2005 |
| WO | WO2006112283 A1 | 10/2006 |
| WO | 2009/065119 A2 * | 5/2009 |

OTHER PUBLICATIONS

International Search Report for PCT/US2008/083762.
Wikipedia "Red Bull" http://en.wikipedia.org/wiki/Red_Bull.
Frequently Asked Questions about 5-Hour Energy, http://www.5hourenergy.com/QandA.asp, pp. 1-3.
Flashup Drink, Disclosure from the Russian Patent Office 1999.
International Report on Patentability for WO2009065119, Nov. 17, 2008.
Driskell et al, Sports Nutrition:Vitamins and Trace Elements, Second Edition. 2006, pp. 146-148.
Wikipedia "Red Bull" http://en.wikipedia.org/wiki/Red_Bull, 2009.
5-Hour Energy Ingredients & Safety, 2011, http://www.5hourenergy.com/ingredients.asp, pp. 1-3.
Frequently Asked Questions about 5-Hour Energy, http://www.5hourenergy.com/QandA.asp, pp. 1-3, 2011.
European Search Report for European Patent Application 08850385.9, Apr. 14, 2014.
International Search Report for PCT/US2008/083762, Jul. 2, 2009.
Wikipedia "Red Bull" http://en.wikipedia.org/wiki/Red_Bull, 1987.
5-Hour Energy Ingredients & Safety, 2007, http://www.5hourenergy.com/ingredients.asp, pp. 1-3.
Frequently Asked Questions about 5-Hour Energy, http://www.5hourenergy.com/QandA.asp, pp. 1-3, Nov. 24, 2005.

* cited by examiner

*Primary Examiner* — Helen F Heggestad
(74) *Attorney, Agent, or Firm* — Oakland Law Group PLLC

(57) ABSTRACT

The disclosure relates to an edible energy composition that includes a methylated xanthine, a choline derivative and a flavorant.

10 Claims, No Drawings

EDIBLE ENERGY COMPOSITION

CROSS-REFERENCE TO RELATED APPLICATION

This application is a continuation-in-part of prior application Ser No. 12/139,163, filed Jun. 13, 2008 which is hereby incorporated by reference in its entirety.

BACKGROUND

There are a number of products that purport to provide an individual with physical and mental benefits when consumed. These products are often packaged as solid snack foods or as drinks and are consumed by individuals wanting to quickly increase and/or maintain their physical energy and mental alertness in particular situations. For example, students may take the products to study for longer periods, athletes may consume them to train or compete and employees may take them during the work day.

However, these products may include undesirable amounts of calories due to, for example, the inclusion of sugars, and/or may provide an unpleasant taste and/or may fail to provide sufficient physical and mental benefits for an adequate period of time. Moreover, consumers continually desire palatable, unique and healthy formulations. Accordingly, there is a need for improved edible compositions that provide consumers with benefits such as increased energy and alertness.

SUMMARY

The present invention describes an edible energy composition that includes a methylated xanthine in an amount from about 0.05% to about 0.5%, a choline derivative in an amount from about 0.005% to about 0.09% (w/w), and at least one flavorant.

The present invention also describes an edible energy composition that includes methylated xanthine, a choline derivative, amino acids, vitamins, taurine, acidulants and at least one flavorants and where consumption of said composition provides a user with at least one benefit such as increased alertness, increased mental acuity, increased continuity of attention and increased self-related awareness.

The present invention also relates to an edible energy composition that includes a methylated xanthine, a choline derivative, amino acids, vitamins, taurine, glucuronolactone, acidulants and at least one flavorant.

DETAILED DESCRIPTION

It is to be understood that the disclosed embodiments are merely exemplary and details disclosed herein are not to be interpreted as limiting, but merely as a representative basis for teaching one skilled in the art.

The disclosure relates to a stable, edible energy composition. The composition may be in liquid or solid form or include both liquid and solid forms. The composition may be provided in any mass or volume. For example, the composition may be provided as a solid food item in the form of bars, crackers, cookies or similar products, having the mass and shape of these types of products. The composition may also be provided as a liquid consumable such as a "shot", drink, beverage or gel, which may be served at a wide range of temperatures from freezing (0° C.) to up to about 90° C. In its various forms, the composition is stable and edible for at least two years and may be stable and edible up to about five years.

The use of the composition provides certain benefits. For example, the composition may counter, reduce or prevent drowsiness. The composition may also provide a feeling of alertness and mental acuity. The composition may also provide a significant increase in the power of attention, continuity of attention, quality of working memory, quality of episodic memory, speed of memory and self-related alertness, the sum of the benefits providing a perceived feeling of energy.

The cognitive and physiological effects of the composition are sustained for an extended period of time. The effect of the composition on alertness and energy is greater than would be observed than when ingesting an equivalent amount of any if the ingredients alone. Referring specifically to caffeine, the benefits are sustained longer than the time for the peak plasma concentration of caffeine to be achieved when caffeine is consumed alone. In one embodiment, the composition may provide benefits for least five hours, longer than the effects of an equivalent amount of caffeine taken alone. In other words, the ingredients of the composition act synergistically to produce benefits to a consumer that exceed the benefits achieved when the ingredients are taken individually.

In preferred embodiments, the composition may be provided in an aqueous medium in a volume from about 10 mls to about 300 mls. The composition may be provided in a volume from about 0.3 ounces to about ten (10) ounces. In preferred embodiments, the composition may be provided in about 0.5 fluid ounces, or about one (1) fluid ounce or about two (2) fluid ounces. In a preferred embodiment, the composition is provided as a "shot" where the consumer ingests the ingredients in a small volume, such as from about 55 to about 60 mls and where the ingredients are in a highly concentrated form.

As used herein derivatives are defined to include, but are not limited to, precursors, metabolites, structurally-similar compounds and analogs of a particular substance.

As used herein, precursors of a given substance are defined to include, but are not limited to, molecules that may be transformed, directly or indirectly, into that substance in vivo or in vitro.

As used herein, metabolites of a substance are defined to include, but are not limited to, molecules that are produced in vivo by transformation of that substance.

As used herein, structurally similar-compounds are defined to include, but are not limited to, molecules that are structurally similar to the identified substance but possess at least one structural difference and are functionally similar.

As used herein, analogs are defined to include, but are not limited to molecules that are chemically distinct from an identified substance but which exert the same biological activity.

The energy composition includes at least one methylated xanthine and at least one choline derivative including precursors, structurally-similar compounds, analogs and/or metabolites of these substances. The composition may also include vitamins, amino acids, taurine, glucuronolactone, glucono-delta-lactone, and glucuronic acid, flavorants, sweeteners and preservatives, including precursors, structurally-similar compounds, analogs and/or metabolites of these substances.

Methylated xanthines include but are not limited to caffeine, theobromine, aminophylline, theophylline and paraxanthine. In general, methylated xanthines induce a feeling of alertness when ingested. In one model, methylated xanthines competitively block the binding of adenosine to its target sites in the human nervous system. Consequently, the mood-altering and sleep-inducing effects of adenosine are mitigated and xanthines thus prevent the body from being affected by the depressing effects of adenosine.

Choline is used in the synthesis of phospholipids, phosphatidylcholine and sphingomyelin, structural components of all cell membranes. Choline is also involved in cell signaling. For example, phosphatidylcholine and sphingomyelin are precursors for the intracellular messenger molecules, diacylglycerol and ceramide. Choline is required for the synthesis of platelet activating factor (PAF) and sphingophosphorylcholine, which are also cell-signaling molecules. Choline is also a precursor for acetylcholine, an important neurotransmitter involved in muscle control, memory and mood. Supplementation with choline is implicated in improved cognition, memory and learning and may provide neuroprotective benefits.

Choline is oxidized in the body to form betaine which is a source of methyl ($CH_3$) groups required for methylation reactions. For example, methyl groups from betaine may be used to convert homocysteine to methionine, thereby reducing homocysteine levels. Elevated levels of homocysteine in the blood have been associated with increased risk of cardiovascular diseases.

The composition may include at least one vitamin. For example, the composition may include vitamin B6. Vitamin B6, in its various forms, is involved in more than 100 enzymatic reactions involved in amino acid metabolism and the metabolism of one-carbon units, carbohydrates, and lipids. Vitamin B6 is also required for the biosynthesis of neurotransmitters. In the brain, the synthesis of the neurotransmitter serotonin from the amino acid tryptophan is catalyzed by a vitamin B6-dependent enzyme. Other neurotransmitters, such as dopamine, norepinephrine and gamma-aminobutyric acid (GABA), are also synthesized using vitamin B6-dependent enzymes. Vitamin B6 functions as a coenzyme in the synthesis of heme, an iron-containing component of hemoglobin.

In addition the amount of homocysteine in the blood is regulated by at least three vitamins: folic acid, vitamin B12, and vitamin B6. Several large studies have demonstrated an association between low vitamin B6 intake or status with increased blood homocysteine levels and increased risk of cardiovascular diseases Vitamin B6 is also involved in gluconeogenesis, glycogenolysis and immune function. It serves as a coenzyme for a key enzyme involved in the mobilization of single-carbon functional groups (one-carbon metabolism) including reactions that are involved in the synthesis of nucleic acids. The effect of vitamin B6 deficiency on the function of the immune system may be partly related to its role in one-carbon metabolism.

The binding of vitamin B6 to steroid receptors for estrogen, progesterone, testosterone, and other steroid hormones suggests that the vitamin B6 status of an individual may have implications for diseases affected by steroid hormones, including breast cancer and prostate cancer.

In some embodiments, the composition may include folate. Folate is required for DNA and RNA synthesis. Folate is required to make normal red blood cells and to prevent anemia. Folate is also essential for the metabolism of homocysteine, helping to maintain normal levels of this amino acid. A deficiency of folate, vitamin B12 or vitamin B6 may increase blood levels of homocysteine, and folate supplementation has been shown to decrease homocysteine levels and to improve endothelial cell function. At least one study has linked low dietary folate intake with an increased risk of coronary events.

Some evidence associates low blood levels of folate with a greater risk of cancer, possibly through increased DNA damage that may lead to cancer.

In some embodiments, the composition includes vitamin B12. Vitamin B12 exists in several forms containing the mineral cobalt, e.g. methylcobalamin and 5-deoxyadenosylcobalamin. Vitamin B12 is required for proper red blood cell formation, neurological function, and DNA synthesis. Vitamin B12 functions as a cofactor for two enzymes that catalyze the conversion of homocysteine to methionine. Methionine, in turn, is required for the formation of S-adenosylmethionine, a universal methyl donor for almost 100 different substrates, including DNA, RNA, hormones, proteins, and lipids. Methylation of DNA may be important in cancer prevention. Inadequate function of methionine synthase can lead to an accumulation of homocysteine, which has been associated with increased risk of cardiovascular diseases.

The composition may include niacin, also known as nicotinic acid or vitamin B3 and derivatives of niacin, including precursors, structurally related compounds, analogs and metabolites. Nicotinamide used by the body to form the coenzymes nicotinamide adenine dinucleotide (NAD) and nicotinamide adenine dinucleotide phosphate (NADP) which are used in numerous enzymatic reactions, mainly to accept or donate electrons for redox reactions. NAD functions most often in energy producing reactions involving the catabolism of carbohydrates, fats, proteins, and alcohol. NADP functions more often in biosynthetic (anabolic) reactions. Cellular NAD is consumed in the synthesis of ADP-ribose polymers, which play a role in DNA repair, and cyclic ADP-ribose may also mediate cell-signaling pathways important in cancer prevention. Moreover, one study reported that niacin supplementation decreased the risk of ultraviolet light-induced skin cancers in mice.

Taurine is involved in numerous biological processes including cardiovascular regulation, antioxidation, and modulation of ion transport, membrane stabilization, and osmoregulation, modulation of neurotransmission, bile acid conjugation, hypolipidemia and antiplatelet activity. Deficiency of taurine is linked to retinal degeneration, retardation of growth and development central nervous system disorders, cardiovascular dysfunction, immune disorders and hepatic disorders. Taurine helps regulate the contraction and pumping action of the heart muscle and it helps regulate blood pressure and platelet aggregation.

The composition may include one or more amino acids, including, without limitation, precursors, structurally-similar compounds, analogs, metabolites, salts, esters or isomeric forms of amino acids. In addition to being incorporated into proteins, amino acids play numerous roles in physiological processes and supplementation with amino acids has been studied in numerous contexts. For example, phenylalanine is an essential amino acid and plays a key role in the biosynthesis of other amino acids and some neurotransmitters. Similarly, tyrosine is required for the synthesis of adrenal hormones epinephrine, norepinephrine, dopamine and the thyroid hormones, including thyroxine. Tyrosine, through its effect on neurotransmitters, is used to treat conditions including mood enhancement, appetite suppression, and growth hormone (HGH) stimulation. Tyrosine is also involved in the production of melanin, the pigment responsible for hair and skin color.

Embodiments of methylated xanthines include but are not limited to caffeine theobromine, aminophylline, theophylline and paraxanthine and includes precursors, structurally-similar compounds, analogs and metabolites of methylated xanthines. In one embodiment, the methylated xanthine is present in an amount from about 0.05% to about 0.5% by weight (i.e. w/w) (or for some liquid forms from about 0.0005 g/ml to about 0.005 g/ml). In another embodiment, the methylated xanthine is present in an amount from about 0.35% to about 0.45% w/w (or from about 0.0035 g/ml to about 0.0045 g/ml). In still other embodiments, the methylated xanthine is present in an amount from about 0.37% to about 0.39% (or from about 0.0037 g/ml to about 0.0039 g/ml) or the methylated xanthine is present in an amount from about 0.32% to about 0.34% by weight (or from about 0.0032 g/ml to about 0.0034 g/ml).

The choline derivatives, including precursors, structurally-similar compounds, analogs and metabolites of choline may include but are not limited to choline, citicholine, phosphocholine, and betaine and phosphatidyl choline. In a preferred embodiment, the choline derivative is citicoline. In one embodiment, the choline derivative is present in an amount from about 0.005% to about 0.09% by weight or from about 0.00005 g/ml to about 0.0009 g/ml. In another embodiment, the choline derivative is present in an amount from about 0.03% to about 0.07% by weight or from about 0.0003 g/ml to about 0.0007 g/ml. In still another embodiment, the choline derivative is present in an amount from about 0.04% to about 0.06% by weight (or from about 0.0004 g/ml to about 0.0006 g/ml). In still another embodiment, the choline derivative is present in an amount from about 0.015% to about 0.019% (or from about 0.00015 g/ml to about 0.00019 g/ml).

The energy composition may further include one or more amino acids including, without limitation, precursors, structurally-similar compounds and analogs, metabolites, salts, esters or isomeric forms of amino acids. In preferred embodiments, the amino acids include, but are not limited to, N-acetyl L-tyrosine, tyrosine and phenylalanine. In one embodiment, amino acids are present in an amount from 0.5% to 5.0% by weight or from about 0.005 g/ml to about 0.05 g/ml. In one embodiment, amino acids are present in an amount from about 1% to about 4% by weight (or from about 0.01 to about 0.04 g/ml). In still another embodiment, amino acids are present in an amount from about 1% to about 3% by weight (or from about 0.01 g/ml to about 0.03 g/ml). Examples of other amino acids that may be used, without limitation, include theanine, glutamic acid, alanine and β-alanine.

In a preferred embodiment, the edible composition includes N-acetyl L-tyrosine in an amount from about 0.1% to about 0.8% by weight (or about 0.001 to about 0.008 g/ml). In another embodiment, N-acetyl L-tyrosine is present in an amount from 0.2% to about 0.6% (or from about 0.002 g/ml to about 0.006 g/ml). In still another embodiment, N-acetyl L-tyrosine is present in an amount from about 0.3% to about 0.5% by weight (or from about 0.003 g/ml to about 0.005 g/ml).

The composition may also include phenylalanine. In one embodiment, L-phenylalanine is present in an amount from about 0.1% to about 0.8% by weight (or from about 0.001 to about 0.008 g/ml). In one embodiment, L-phenylalanine is present in an amount from about 0.2% to about 0.6% by weight (or from about 0.002 to about 0.006 g/ml). In still another embodiment, L-phenylalanine is present in an amount from about 0.3% to about 0.5% (or about 0.003 to about 0.005 g/ml).

The composition may also include taurine, including derivatives of taurine which may include precursors, structurally-similar compounds, analogs and/or metabolites. In one embodiment, taurine is present in an amount from about 0.2% to about 1.6% by weight (or from about 0.002 g/ml to about 0.016 g/ml). In one embodiment, taurine is present in an amount from about 0.4% to about 1.2% by weight (or from about 0.004 g/ml to about 0.012 g/ml). In still another embodiment, taurine is present in an amount from about 0.7% to about 1.0% (or from about 0.007 g/ml to about 0.010 g/ml)

In further embodiments, the energy composition includes additional components that may reduce fatigue and provide energy. Such additional components may include, for example, one or more of glucuronolactone, glucono delta-lactone, and glucuronic acid. In one embodiment, glucuronolactone is present in an amount from about 0.1% to about 1.2% (or from about 0.001 g/ml to about 0.012 g/ml). In a further embodiment, glucuronolactone is present in an amount from about 0.003 to about 0.09%. (or from about 0.00003 g/ml to about 0.0009 g/ml). In still another embodiment, glucuronolactone is present in an amount from about 0.5% to about 0.7% (or from about 0.005 g g/ml to about 0.007 g/ml). The composition may also include malic and/or citric acid. Citric and malic acid are intermediates in the conversion of food to energy e.g. they are part of the citric acid cycle.

In one embodiment, the pH of the composition is from about 1.0 to about 9.0. In a preferred embodiment, the pH of the composition is acidic. For example, the pH may be from about 2.0 to about 3.0. The energy composition may further include one or more pH-modifying components. In one embodiment, the pH-modifying components are acidulants. Suitable pH-modifying components include edible inorganic acids, such as phosphoric acid. In preferred embodiments, the composition includes edible organic acids. Preferred embodiments of edible organic acids include malic acid and citric acid.

In one embodiment, the pH-modifying components are present in an amount from about 0.10% to about 1.2% or from about 0.001 g/ml to about 0.012 g/ml. In one embodiment, the pH-modifying components are present in an amount from about 0.3% to about 0.9% (or from about 0.003 to about 0.009 g/ml). In still another embodiment, the pH-modifying components are present in an amount from about 0.5 to about 0.7% (or from about 0.005 g/ml to about 0.007 g/ml).

In preferred embodiments, the energy composition further comprises one or more vitamins, including, without limitation, precursors, structurally-similar compounds, analogs, metabolites, isomers, salts of vitamins. Embodiments of such include, but are not limited to B6, B12, niacinamide niacin and folic acid. In one embodiment, vitamins are present in an amount from about 0.05% to about 0.8% or from about 0.0005 g/ml to about 0.008 g/ml. In another embodiment, vitamins are present in an amount from about 0.1% to about 0.5% or from about 0.001 g/ml to about 0.005 g/ml. In still another embodiment, vitamins are present in an amount from about 0.10% to about 0.25% (or from about 0.001 g/ml to about 0.0025 g/ml).

The energy composition may include vitamin B6. In one embodiment, the B6 is present in an amount from about 0.01% to about 0.3% or from about 0.001 g/ml to about 0.003 g/ml). In another embodiment, the vitamin B6 is present in an amount from about 0.03% to about 0.2% (or from about 0.0003 g/ml to about 0.002 g/ml). In still another embodiment, the vitamin B6 is present in an amount from about 0.06% to about 0.09% (or from about 0.0006 g/ml to about 0.0009 g/ml). The composition may provide from about 50% to about 3000% of the recommended daily allowance of vitamin B6.

The energy composition may include vitamin B12. In one embodiment, the B12 is present in an amount from about 0.0001% to about 0.003% (or from about 0.00001 g/ml to about 0.00003 g/ml). In another embodiment, the B12 is present in an amount from about 0.0003% to about 0.002% (or from about 0.00003 g/ml to about 0.00002 g/ml). In still another embodiment, the B12 is present in an amount from about 0.0006% to about 0.001% (or from about 0.000006 g/ml to about 0.00001 g/rin1). The composition may provide from about 50% to about 10000% of the recommended daily allowance of vitamin B12.

The energy composition may include niacin and/or niacinamide. In one embodiment, niacinamide is present in an amount from about 0.00001% to about 0.3% (or from about 0.0000001 g/ml or from about 0.003 g/ml). In one embodiment, the niacinamide or a derivative thereof is present in an amount from about 0.01% to about 0.3% (or about 0.0001 g/ml to about 0.003 g/ml). In another embodiment, the niacinamide or a derivative thereof is present in an amount from about 0.03% to about 0.2% (or about 0.0003 g/ml to about 0.002 g/ml). In still another embodiment, the niacinamide or a derivative thereof is present in an amount from about 0.06% to about 0.09% (or about 0.0006 g/ml to about 0.0009 g/ml). The composition may provide from about 20% to about 300% of the recommended daily allowance of niacin.

The energy composition may include folic acid. In one embodiment, the folic acid is present in an amount from about 0.00001% to about 0.02% (or about 0.0000001 g/ml to about 0.0002 g/ml). In another embodiment, the folic acid is present in an amount from about 0.0005% to about 0.02% (or about 0.000005 g/ml to about 0.0002 g/ml). In another embodiment, the folic acid is present in an amount from about 0.001% to about 0.008% (or about 0.00001 g/ml to about 0.00008 g/ml). In still another embodiment, the folic acid is present in an amount from about 0.002% to about 0.004% (or about 0.00002 g/ml to about 0.0004 g/ml). The composition may provide from about 10% to about 100% of the recommended daily allowance of folic acid.

The energy composition of the present embodiment includes one or more flavorants and/or sweeteners. In one embodiment, there are a sufficient number of flavorants and/or sweeteners so that unpalatable tasting components will be masked. In one embodiment, the flavorants are present in an amount from about 0.0001% to about 0.8% (or about 0.0000001 g/ml to about 0.008 g/ml). In another embodiment, the flavorants are present in an amount from about 0.1% to about 0.8%.

According to the disclosure, nutritive or non-nutritive sweeteners may be added. Examples of such sweeteners include, but are not limited to xylitol, stevia, aspartame, sucralose and other non-nutritive sweeteners known to those of ordinary skill in the art. In one preferred embodiment, sucralose is may be used. In a further embodiment, sucralose is present in an amount from 0.001% to about 0.4% (or about 0.00001 g/ml to about 0.004 g/ml). In one embodiment, sucralose is present in an amount from about 0.05% to about 0.4% (or about 0.0005 g/ml to about 0.004 g/ml). In one embodiment, sucralose is present in an amount from about 0.08% to about 0.3% (or about 0.0008 g/ml to about 0.003 g/ml). In still another embodiment, sucralose is present in an amount from about 0.1% to about 0.2% (or about 0.001 g/ml to about 0.002 g/ml).

In some embodiments, preservative agents may be added to the composition. Ethylene diamine tetraacetic acid ("EDTA") may also be included to improve flavor and stability. In one embodiment, EDTA is present in an amount from about 0.002% to about 0.009% (or about 0.00002 g/ml to about 0.00009 g/ml). In another embodiment, the EDTA is present in an amount from about 0.003% to about 0.007% (or about 0.00003 g/ml to about 0.000007 g/mp). In still another embodiment, the EDTA is present in an amount from about 0.004% to about 0.006% (or about 0.00004 g/ml to about 0.00006 g/ml). In still another embodiment, the EDTA is present in an amount from about 0.002% to about 0.003% (or about 0.00002 g/ml to about 0.00003 g/ml). The energy composition also includes one or more fruit flavorants. Such fruit flavorants include, but are not limited to lemon lime flavors, orange flavors, berry flavors, high fructose corn syrup, raspberry juice concentrates, berry juice concentrates and the like.

In still another variation of the present embodiment, the energy composition further includes one or more enzymes. Embodiments of such enzymes include, but are not limited to, amylase, protease, lactase, lipase, cellulase, and combinations thereof.

The energy composition may also include added fiber. Cellulose is an example of a fiber that may be used in the present variation.

The energy composition may further include at least one preservative. In one embodiment, the preservative is a natural preservative. Embodiments of useful preservatives include, but are not limited to, benzoic acid and benzoic acid derivatives such as sodium benzoate, calcium benzoate, potassium benzoate, magnesium benzoate, and combinations thereof. The preservative may include sorbic acid derivatives such as potassium sorbate. In one embodiment, the preservative is present in an amount from about 0.01% to about 1.0% (or from about 0.0001 g/ml to about 0.01 g/ml). In one embodiment, the preservative is present in an amount from about 0.1% to about 0.8%.

The composition provides food energy, i.e. provides calories. In preferred embodiments, the composition provides a relatively small amount of food energy. For example, the composition may provide less than about 0.1 kcal/g (or kcal/ml), or less than about 0.2 kcal/g or (kcal/ml) or less than about 0.3 kcal/g (or kcal/ml) of food energy. In one embodiment, the composition provides about four (4) kcal in about 55 to 60 mls. In preferred embodiments, the composition does not contain sugars such as glucose, lactose, sucrose or fructose.

Tables 1-5 provide a set of components that may be introduced into such a liquid. The amounts provided in tables 1-5 are particularly useful to form compositions having a total final volume of about 2 fluid ounces.

TABLE 1

| Component | Amount (mg) |
| --- | --- |
| Caffeine | 8-220 |
| Citicoline | 5-30 |
| Vitamins B6 | 20-60 |
| Vitamins B12 | 0.30-0.70 |
| Niacinamide | 0-60 |
| Folic Acid | 0-5 |
| Glucuronolactone | 200-600 |
| N-Acetyl L-Tyrosine | 150-500 |
| L-Phenylalanine | 150-400 |
| Taurine | 300-800 |
| Malic Acid | 200-500 |
| Flavorants | 0-400 |
| Sodium benzoate | 0-150 |
| potassium sorbate | 0-150 |
| Sucralose | 0-150 |

TABLE 2

| Component | Amount (mg) |
| --- | --- |
| Caffeine | 100-200 |
| Citicoline | 1-25 |

TABLE 2-continued

| Component | Amount (mg) |
| --- | --- |
| Vitamins B6 | 35-45 |
| Vitamins B12 | 0.50 |
| Niacinamide | 35-45 |
| Folic Acid | 0.1-0.7 |
| Glucuronolactone | 300-500 |
| N-Acetyl L-Tyrosine | 200-400 |
| L-Phenylalanine | 200-400 |
| Taurine | 350-700 |
| Malic Acid | 200-500 |
| Flavorants | 0-400 |
| Sodium benzoate | 0-150 |
| potassium sorbate | 0-150 |
| Sucralose | 0-150 |

TABLE 3

| Component | Amount (mg) |
| --- | --- |
| Caffeine | 100-250 |
| Citicoline | 10-50 |
| Vitamins B6 | 20-60 |
| Vitamins B12 | 0.30-0.70 |
| Niacinamide | 0-60 |
| Folic Acid | 0-5 |
| Glucuronolactone | 200-600 |
| N-Acetyl L-Tyrosine | 150-500 |
| L-Phenylalanine | 150-400 |
| Taurine | 300-800 |
| Malic Acid | 200-500 |
| Flavorants | 0-400 |
| Sodium benzoate | 0-150 |
| potassium sorbate | 0-150 |
| Sucralose | 0-150 |

TABLE 4

| Component | Amount (mg) |
| --- | --- |
| Caffeine | 100-230 |
| Citicoline | 20-45 |
| Vitamins B6 | 35-45 |
| Vitamins B12 | 0.20-0.75 |
| Niacinamide | 35-45 |
| Folic Acid | 1-2 |
| Glucuronolactone | 300-500 |
| N-Acetyl L-Tyrosine | 200-400 |
| L-Phenylalanine | 200-400 |
| Taurine | 300-800 |
| Malic Acid | 250-500 |
| Flavorants | 200-350 |
| Sodium benzoate | 25-75 |
| potassium sorbate | 25-75 |
| Sucralose | 75-150 |

TABLE 5

| Component | Amount (mg) |
| --- | --- |
| Caffeine | 100-230 |
| Citicoline | 20-45 |
| Vitamins B6 | 35-45 |
| Vitamins B12 | 0.25-0.75 |
| Niacinamide | 35-45 |
| Folic Acid | 1-2 |
| Glucuno delta lactone | 300-500 |
| N-Acetyl L-Tyrosine | 200-400 |
| L-Phenylalanine | 200-400 |
| Taurine | 350-700 |
| Malic Acid | 250-400 |
| Flavorants | 0-400 |
| Sodium benzoate | 0-150 |
| potassium sorbate | 0-150 |
| Sucralose | 0-150 |

It is to be understood that this disclosure is not limited to the embodiments described above as specific components and conditions may vary. Furthermore, the terminology used herein is used only for the purpose of describing particular embodiments and is not intended to be limiting in any way.

The invention claimed is:

1. An edible energy composition consisting of:
a methylated xanthine;
a choline derivative;
taurine;
vitamin B6, vitamin B12, folic acid, niacin;
N-acetyl-tyrosine;
L-phenylalanine,
an organic acid;
glucuronolactone;
a non-nutritive sweetener;
and at least one flavorant
wherein the composition provides from about 0.1 calories to about 10 calories in about 10 to about 300 ml.

2. The edible energy composition of claim 1 wherein said vitamin B6 is present in an amount from about 0.01% to about 0.3%; said vitamin B12 is present in an amount from about 0.0001% to about 0.003%; said folic acid is present in an amount from about 0.0005% to about 0.02%; and said niacinamide is present in an amount from about 0.01% to about 0.3%.

3. The edible energy composition of claim 1 wherein said methylated xanthine is caffeine.

4. The edible energy composition of claim 1 wherein said choline derivative is citicoline.

5. The edible energy composition of claim 1 wherein said non-nutritive sweetener is sucralose present in an amount from about 0.001% to about 0.4%.

6. The edible energy composition of claim 1 wherein the composition provides about 4 calories in about 2 fluid ounces.

7. The edible energy composition of claim 1 wherein said composition has an acidic pH.

8. The edible energy composition of claim 1 wherein said composition has a pH from about 02.0 to about 3.0.

9. The energy composition of claim 1 further-wherein said glucuronolactone in an amount from about 0.1% to about 1.2%.

10. The edible energy composition of claim 1 wherein N-acetyl L-tyrosine is present in an amount from about 0.1% to about 0.8%, L-phenylalanine in an amount from about 0.1 to about 0.8% and taurine in an amount from about 0.1% to about 0.8%.

* * * * *